United States Patent [19]

Self

[11] Patent Number: 4,595,655
[45] Date of Patent: * Jun. 17, 1986

[54] ASSAY METHOD AND REAGENT THEREFOR

[76] Inventor: Colin H. Self, 46 Lensfield Road, Cambridge, United Kingdom

[*] Notice: The portion of the term of this patent subsequent to May 1, 2001 has been disclaimed.

[21] Appl. No.: 448,369

[22] Filed: Dec. 9, 1982

Related U.S. Application Data

[63] Continuation of Ser. No. 193,647, Oct. 3, 1980, abandoned.

[30] Foreign Application Priority Data

| Oct. 3, 1979 | [GB] | United Kingdom | 7934376 |
| Mar. 3, 1981 | [GB] | United Kingdom | 8110031 |
| Mar. 7, 1981 | [GB] | United Kingdom | 8107249 |
| Apr. 1, 1981 | [GB] | United Kingdom | 8110233 |

[51] Int. Cl.$^4$ .................... G01N 33/54; C12Q 1/32
[52] U.S. Cl. ........................... 435/7; 435/26; 435/810; 436/518; 436/536; 436/537
[58] Field of Search ............ 435/7, 188, 810, 26; 436/518, 536, 537

[56] References Cited

U.S. PATENT DOCUMENTS

| 3,654,090 | 4/1972 | Schuurs et al. | 435/188 |
| 3,730,844 | 5/1973 | Gilham et al. | 435/6 |
| 3,879,262 | 4/1975 | Schuurs et al. | 435/7 |
| 4,134,792 | 1/1979 | Boguslaski et al. | 435/7 |
| 4,230,797 | 10/1980 | Boguslaski et al. | 435/810 |
| 4,233,402 | 11/1980 | Maggio et al. | 435/7 |
| 4,277,560 | 7/1981 | Gray et al. | 436/807 |
| 4,299,916 | 11/1981 | Litman et al. | 435/810 |
| 4,307,188 | 12/1981 | White | 435/4 |
| 4,318,980 | 3/1982 | Boguslaski et al. | 435/810 |
| 4,366,242 | 12/1982 | Neumann et al. | 435/7 |
| 4,446,231 | 5/1984 | Self | 435/7 |

FOREIGN PATENT DOCUMENTS

| 0005271 | 11/1979 | European Pat. Off. |  |
| 0027036 | 4/1981 | European Pat. Off. |  |
| WO80/02747 | 12/1980 | PCT Int'l Appl. | 435/7 |
| WO81/00725 | 3/1981 | PCT Int'l Appl. | 435/7 |
| 1363565 | 8/1974 | United Kingdom |  |
| 1433783 | 4/1976 | United Kingdom |  |
| 1536396 | 12/1978 | United Kingdom |  |
| 1548741 | 7/1979 | United Kingdom |  |
| 1550320 | 8/1979 | United Kingdom |  |
| 1552607 | 9/1979 | United Kingdom |  |
| 2021262 | 11/1979 | United Kingdom | 435/7 |
| 2034466 | 6/1980 | United Kingdom |  |
| 2001172 | 1/1982 | United Kingdom | 435/7 |

OTHER PUBLICATIONS

Anggard et al, "Prostaglandins: Enzymatic Analysis", Science, 163, pp. 479-480 (1-31-1969).
Analytical Chemistry, vol. 50, No. 8, Jul. 1978, pp. 1026-1032.
Chem. Abstracts 72, 405447b, 1970.
O. H. Lowry, et al, "The Measurement of Pyridine Nucleotides by Enzymatic Cycling", J. Biological Chem., vol. 236, No. 10, 1060, pp. 2746-2755.
E. Pitkanen, "The Hydrolysis of Nicotinamide Adenine Dinucleotide Phosphate by Serum Alkaline Phosphatase", Enzyme, vol. 12, 1971, pp. 226-234.

Primary Examiner—Thomas G. Wiseman
Assistant Examiner—John Edward Tarcza
Attorney, Agent, or Firm—Jacobs & Jacobs

[57] ABSTRACT

The present invention provides a method for determining a ligand or receptor which comprises carrying out an assay for the ligand or receptor, the assay requiring a labelled component, wherein the labelled component is a conjugate between a ligand or a receptor and a primary enzyme that is itself capable of producing or removing a modulator for a secondary system or that is the first enzyme in an enzyme system that is capable of producing or removing a modulator for a secondary system, and determining that portion of labelled component to be determined by allowing the primary enzyme and any other enzymes in the enzyme system, to produce or remove the modulator for the secondary system, allowing the secondary system to function in the presence or absence as appropriate of the modulator, and determining a product of the secondary system.

36 Claims, No Drawings

ASSAY METHOD AND REAGENT THEREFOR

CROSS-REFERENCE

This is a continuation of Ser. No. 193,647 filed Oct. 3, 1980 now abandoned.

The present invention relates to assays which use a reagent that is enzyme-linked.

Various methods are available for the detection and/or identification of substances in, for example, samples of body materials. Immunoassays make use of the specificity of the reaction of an antigen with its antibody for the detection of substances which are antigenic or can be made antigenic or, conversely, are antibodies or derivatives thereof. Immunoassays may be used for the detection of any substance of any origin provided it falls within one of the above categories, and are particularly useful for testing samples of body materials for the detection of various types of substances, especially naturally occurring substances, for example, hormones, the content of which may change under certain circumstances, for example, pregnancy; substances which may be present in the body under certain circumstances but which are not normally present, for example, particular tumour antigens specifically associated with malignant states; and non-naturally occurring substances, for example, certain drugs.

As indicated above, immunoassays may also be used for the detection of antibodies rather than antigens, for example, in autoimmune diseases and certain cancers, and also to detect certain infectious diseases which give rise to altered specific antibody titres in affected individuals. In the latter case, the disease may be detected and, if desired, its course followed while present in the individual to monitor, for example, response to treatment, or previous infection may be detected, for example, in the testing for rubella.

Immunoassays may be used for qualitative or quantitative determinations. Colour reactions and precipitation reactions, for example, using latex particles for visualisation, are often used in qualitative methods to indicate the presence or absence of the substance under investigation.

In quantitative assays, one of the components is usually labelled in some way, for example, with a radioisotope or with a fluorescent group. Radioactive labels have a number of disadvantages, however, including the cost and complexity of measuring equipment (when compared with colourimetric assays), health hazards associated with radioisotopes, the real limit to sensitivity caused by the degree to which radioisotopes may be incorporated in antigens and antibodies and the inevitable decay of the label on storage.

Similarly, fluorescent labels also require expensive equipment for their determination, and have the further disadvantage that immunofluorescent assays are particularly difficult to standardise and to quantitate. The assessment of results is very subjective and can result in an unacceptable degree of variation among workers.

Other physical and physico-chemical methods are also available for the detection of further types of labels for antibodies and antigens, but these often have limited applicability and again require specialised and expensive apparatus.

Attempts have been made to get round the problems associated with radioisotope and fluorescent labels by the use of enzymes as labels. The enzymes previously proposed have been chosen for their ability to catalyse reactions which are relatively easy to measure and which also proceed at a high rate (cf. Engrall, E. and Perlmann, P., (1972). The Journal of Immunology 109, 129). The enzymes proposed are, for example, those which generate a coloured end product or which produce a substrate for a second enzyme, which substrate is used up in the generation of a coloured end product.

There is, however, the problem of introducing the enzyme label in a high enough concentration and also the problem that simply attaching an enzyme to an antibody or an antigen may result in a certain loss of catalytic activity. The number of labelled molecules to be detected may be relatively small, so it is important that the label can be detected easily.

As indicated above, immunoassays utilise the specificity of the interaction between antibodies and antigens to detect and/or determine these substances. There are, moreover, other analogous pairs of substances that have an analogous specificity for each other; these are the receptors that occur in the body, often in association with cells, and their complementary partners. There is considerable overlap between antibodies and antigens and other ligands and receptors, e.g. a substance that is an antigen may also be the partner for a non-antibody receptor. Moreover, it has proved difficult to distinguish some lymphoid cell receptors from antibody molecules. Examples of partners for non-antibody receptors are substances produced by the body itself, for example, hormones, opiates, and chemical intermediates in the nervous system, and materials originating exterally, for example, viruses and toxins. These receptors and their partners recognise each other and bind specifically with one another in the same manner as do antibodies and antigens, and they can be used in assays that are directly analgous to immunoassays for the detection and/or determination of either partner.

The present invention is based on the observation that the enzyme used as the label in an immunoassay or analogous assay may be an enzyme that produces, directly or indirectly, a substance that is capable of influencing a catalytic event without itself being consumed during the catalytic event.

The invention accordingly provides a method for determining a ligand or receptor, which comprises carrying out an assay for the ligand or receptor, the assay requiring a labelled component, wherein the labelled component is a conjugate between (i) a ligand or a receptor and (ii) a primary enzyme that is itself capable of producing or removing a modulator (as hereinafter defined) for a secondary system or that is the first enzyme in an enzyme system that is capable of producing or removing a modulator (as hereinafter defined) for a secondary system, and determining that portion of labelled component to be determined by allowing the primary enzyme and any other enzymes in the enzyme system, to produce or remove the modulator for the secondary system, allowing the secondary system to function in the presence or absence (as appropriate) of the modulator, and determining a product of the secondary system. By producing or removing as appropriate the modulator, amplification is acheived by the production of substantially more than one molecule of product of the secondary system per molecule of modulator.

The terms "ligand" and "receptor" are used in the present Specification to denote a complementary pair of substances that are capable of recognising the specific spatial and charge configuration of each other and of binding specifically with each other.

Ligands are, for example, antigens, haptens, and the partners of cell- and non-cell associated, non-antibody receptors, and receptors are, for example, antibodies and non-cell and cell-associated non-antibody receptors. The term "non-antibody" receptors as used herein includes non-antibody receptors obtained from natural sources and those produced synthetically or semi-synthetically, and also includes analogues thereof that are capable of binding to the appropriate partner. Similarly, their respective partners may be obtained from natural sources, or may be synthetic or semi-synthetic, or analogues of natural partners provided that they are capable of binding to the appropriate receptor.

The antibody component of an antibody-enzyme conjugate of the invention may be any immunoglobulin obtained from any source, provided that it is suitable for taking part in the desired assay. In some cases, it may be preferable to use a heterogeneous antibody population, for example, as obtained from a whole blood sample, whereas in other cases it may be preferable to use monoclonal antibodies. Furthermore, there may be used mixed antibodies, that is to say, antibodies having light and heavy chains originating in different molecules, the mixed antibodies being produced by hybridisation.

It will be appreciated that, instead of being bound to a complete immunoglobulin molecule, the enzyme may be bound to a suitable immunoglobulin fragment. Accordingly, the term "antibody" when used herein denotes any immunoglobulin molecule or any fragment of an immunoglobulin molecule containing an intact antigen binding site and being capable of being bound to the enzyme without substantially interfering with the antigen binding. Examples of suitable immunoglobulin fragments are Fab and (Fab$^1$)$_2$ fragments.

The antigen component of an antigen-enzyme conjugate of the invention is any antigen that is capable of being bound to the enzyme without substantially interfering with its antibody binding capacity. The term "antigen" when used in the present specification includes haptens, and "antigen-enzyme conjugate" includes hapten-enzyme conjugate, unless otherwise indicated.

The term "modulator" is used herein to denote a substance that gives rise to a catalytic event but of which there is no net consumption during the catalytic event.

The term "enzyme" is used herein to denote a particular enzyme activity. (An enzyme may have the form of a discrete molecule or an enzyme complex which may display more than one enzyme activity.)

The term "primary enzyme system" is used in the present specification to denote a system that comprises an enzyme conjugate of the invention and that is capable of producing or removing a modulator for the secondary system. The primary enzyme system may comprise the primary enzyme as the only enzyme, or it may comprise a series of enzymes of which the primary enzyme is the first.

The term "secondary system" is used herein to denote a reaction or reactions modulated by the product of the primary enzyme system, that is to say, the primary enzyme system produces or removes a substance that, in the presence of the secondary system, gives rise to a catalytic event without being consumed (in net terms) during the catalytic event. An example of a type of modulator that may be produced by the primary enzyme system is an enzyme activator, and enzyme inhibitors are an example of another group of modulators. In the latter case, the primary enzyme system must be capable of removing an inhibitor to "switch on" the secondary enzyme system.

In some cases, the primary enzyme system may be capable of simultaneously producing an activator for a secondary enzyme system and of removing an inhibitor therefor.

An example of a further type of modulator is a substrate or cofactor for a secondary system that is capable of regenerating the substrate or cofactor. Such a secondary system involves a cycle. The modulator "switches on" the cycle, which can then continue to turn almost indefinitely, provided there is a sufficient supply of the appropriate substrates. The cycle comprises two or more reactions, at least one of which may be enzyme catalysed. The other reaction(s) in the cycle may each be enzyme catalysed or not.

The modulator may be physically separated from the secondary system, for example, it may be present in a cell or vesicle. In this case, the primary enzyme system produces the modulator by causing all or some of the modulator to become available to the secondary system, for example, by causing the cell or vesicle to rupture or become permeable The use in assays of the enzyme conjugate of the invention circumvents many of the problems and disadvantages encountered with radioactive and fluorescent labels, and has advantages over previously proposed uses of enzymes as labels, for example, the sensitivity of the assay is improved and the product of the primary enzyme system is not consumed in the reaction for the determination of the label.

By producing or removing a modulator for the secondary system, eg. by producing an activator and/or removing an inhibitor for the secondary enzyme system, or by producing a regeneratable substrate or coenzyme for the secondary enzyme system, or a regeneratable substrate or cofactor for a non-enzymic system, amplification is achieved. Each molecule of modulator results in the production of substantially more than one molecule of product of the secondary system. The modulator produced or removed by the primary enzyme system can be regarded as a catalyst for the secondary system, eg, the presence of an activator or removal of inhibitor "switches on" an enzyme, and a regeneratable substrate or cofactor "switches on" a secondary cycle which can then continue to turn with determinable product being produced at each turn of the cycle. This is in direct contrast to those previous proposed enzyme labels for immunoassays where the enzyme bound in an enzyme conjugate either produces a determinable product directly or produces a substrate for a further enzyme reaction in a simple linear, usually 1:1, ratio. The amplification serves to increase the sensitivity of the assay directly by causing the production of larger numbers of determinable molecules than would be produced directly by ligand or receptor bound enzyme, and thus helps to overcome one of the disadvantages of the previously proposed use of enzymes, that is to say, the tendency to inactivation of certain enzymes on conjugation.

A further advantage is that the reactions involving the primary enzyme system and the secondary system may be carried out separately. This gives greater flexibility with regard to the time and place at which the reactions are carried out. It is also generally easier to quantitate the secondary system if the reactions are carried out separately from those of the primary system. Moreover, there is greater freedom in the choice of enzymes for the secondary system as there can be used in this system enzymes that are not suitable for conjugation to a ligand or receptor, for example, a secondary enzyme system may comprise an insoluble enzyme or an unstable enzyme.

As indicated above, the primary enzyme system used in the method of the invention may comprise the primary enzyme, that is to say, the enzyme present in the conjugate, as the only enzyme, or it may comprise more than one enzyme, only the primary enzyme being bound to a ligand or receptor with each other enzyme generally producing the substrate for the next enzyme. It may be preferable to use a reaction chain as short as possible, for example, using the primary enzyme only to produce or remove the modulator for the secondary enzyme system.

A secondary enzyme system, too, may comprise one or more enzymes. In the case of activation and/or inhibition, there may be only one enzyme in the secondary enzyme system, or the modulated enzyme may be part of a chain or cycle comprising other enzymes and/or non-enzyme catalysed reactions. When the modulator is a regeneratable substrate or cofactor, a cycle is involved. As indicated above, a cycle may comprise at least one enzyme catalysed reaction, or any one or more of the reactions in the cycle may be not catalysed by an enzyme ie a cycle may be wholly chemical; wholly enzymic; or part chemical, part enzymic.

There may be used a secondary enzyme system in which one secondary enzyme produces a substance that is modulatory for a further enzyme, so an extra multiple amplification step is incorporated in the system. Further modulated enzymes and/or modulator-producing enzymes may be used in series.

A secondary enzyme system may be a mixed system comprising enzymes subject to different types of modulation, eg. one or more enzymes subject to activation and/or inhibition, and a cycle capable of regenerating a substrate or coenzyme. This, too, may result in multiple amplification.

The choice of primary enzyme system and secondary system are, of course, linked, as the primary enzyme system must be capable of modulating the secondary system.

Dealing first with the secondary system, this may comprise an enzyme system that is subject to regulation, either by activation or by inhibition. The enzyme system may be naturally subject to regulation or may have been modified to become so. Alternatively, a secondary enzyme system may be capable of regenerating a substrate or cofactor (coenzyme) that is produced by the primary enzyme system and also causing concommitantly the build-up of a substance that is detectable either directly or indirectly. The use of secondary system that generates modulator in this manner is highly advantageous as it may be employed to give rise to a particularly rapid build up in the determinable substance.

A modulator for a secondary system may be natural or synthetic, and a "pre-modulator" may be converted by the primary system into a modulator by removal of the protecting moiety eg. protecting groups or protecting peptides. A natural modulator may have been modified such that it is inactive until acted upon by the primary enzyme system. Metal ions are modulators for some enzymes. A compartmentation system as described below my be used with metal ions.

The secondary system preferably produces a determinable substance or uses a substrate that can be readily determined directly, for example, spectrophotometrically, by colour, by staining, manometrically, by light production eg using ATP on firefly extract, or microbiologically eg by using bacteria with specific nutritional requirements, or by measuring physicochemical changes, eg. conductance changes. The determinable substance produced may, however, be determined indirectly, by acting as the substrate for one or more further reaction(s) producing a readily determinable end product or may be a regulator for a further reaction. An enzyme system may, for example, catalyse a reaction in which carbon dioxide is produced eg. using pyruvate decarboxylase; in which the oxygen tension is changed, eg. using glucose oxidase with measurement by an oxygen electrode; or in which DNP-hydrazine can be used to produce a coloured end product. It is particularly convenient to utilise an enzyme system capable of producing NAD or a compound that can partake in a reaction in which NAD/NADH interconversion is involved. (Abbreviations used in this specification are set out before the Examples.)

Some examples of primary enzyme systems comprising one enzyme only with associated secondary enzyme systems also comprising one enzyme only are given in Table I below, by way of example only:

TABLE I

| Primary enzyme | Secondary enzyme |
| --- | --- |
| 1. Enzyme that produces cyclic AMP eg. adenylate cyclase | Enzyme subject to activation by cyclic AMP eg. phosphorylase B kinase, pyruvate carboxylase, phosphoenol pyruvate kinase |
| 2. Glyoxylate reductase (reduces glyoxylate) | Isocitrate dehydrogenase (inhibited by mixture of glyoxylate and oxaloacetate) |
| 3. Enzyme that removes ATP, especially that converts ATP to ADP eg. ATPase eg. apyrase | Enzyme inhibited by ATP, especially when also activated by ADP eg. isocitrate dehydrogenase |
| 4. Glutathione reductase (produces glutathione) | Glyoxylase (activated by glutathione) |
| 5. Fumarase or fumaryl acetoacetate lyase (produce fumarate) | Mitochondrial NAD-linked malic enzyme (activated by fumarate) |

In the examples given above, the primary enzyme system comprises one enzyme only. As indicated previously, however, the primary enzyme system may comprise several enzymes, only the first being bound in a conjugate. An example of such a system, with a single enzyme in the second system, is given below:

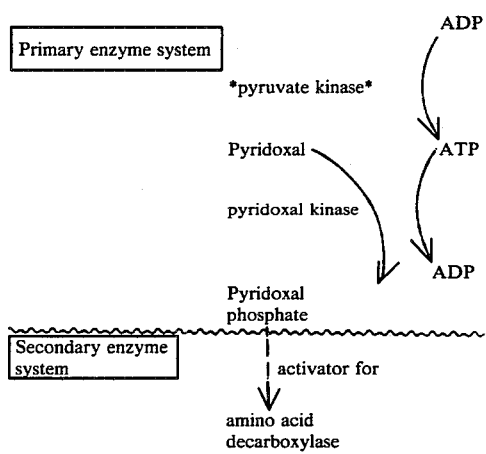

A further example of such a system is the following:

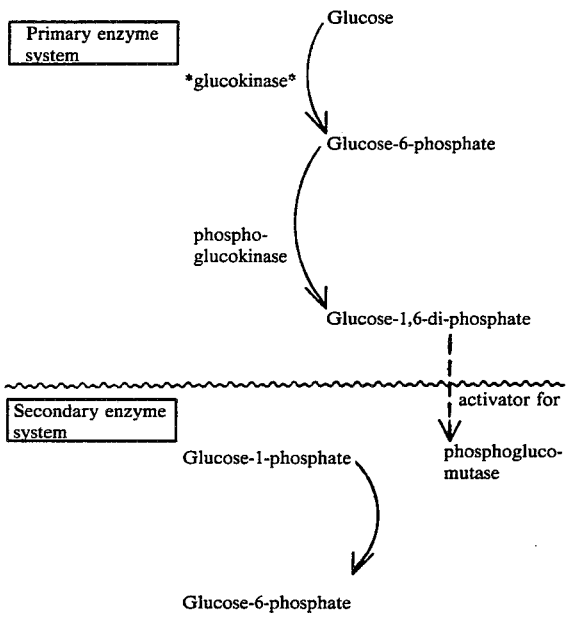

(For this method, the phosphoglucomutase must be in the de-phosphorylated condition. The enzyme can be de-phosphorylated by exposing it to fluoride ions.)

In all diagrams, *...* denotes the primary ie. conjugated enzyme, and there are given only those components of the various reactions that are necessary for the understanding of the reaction schemes.

As indicated previously, a secondary enzyme system may comprise only one enzyme, or it may comprise several enzymes, more than one of which may be subject to regulation by a modulator, if desired. An example of a system comprising a chain of reactions in the secondary system is the following:

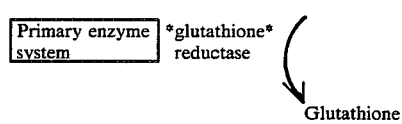

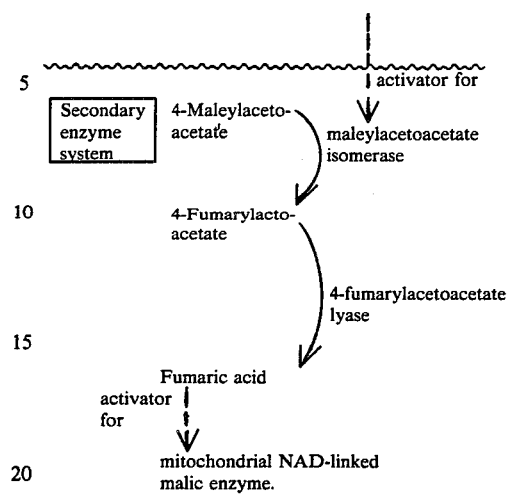

In this case, the product of the primary enzyme system is the modulator for the first enzyme in the secondary enzyme system, and extra multiple amplification is achieved by the inclusion of a further modulated enzyme in the secondary system.

It may be preferable to use primary and secondary enzyme systems as simple as possible. When more enzymes are incorporated, however, particularly if they are themselves subject to modulation, different advantages may be achieved, for example, with regard to the sensitivity of the assay.

An example of a simple system that can be extended with the addition of extra enzymes is that utilising E.coli Type I pyruvate kinase (PK) as the secondary enzyme system with phosphofructokinase as the primary enzyme. Phosphofructokinase produces fructose-1,6-diphosphate (FDP), which is a very potent activator for E.coli Type I pyruvate kinase (in the presence of certain amounts of phosphoenolpyruvate, cf. M. Malcovati, G. Valentini, H. L. Kornberg, Acta vitamin. enzymol. (MIlano) 1973, 27,96.

The system described above can be extended by providing ATP, which is required by phosphofructokinase, indirectly by means of an enzyme capable of converting ATP to ADP, for example, mammalian pyruvate kinase or E.coli Type II pyruvate kinase. Such a system has the advantage that it generates more ATP (the modulator) during the reaction to drive the activator-producing enzyme faster.

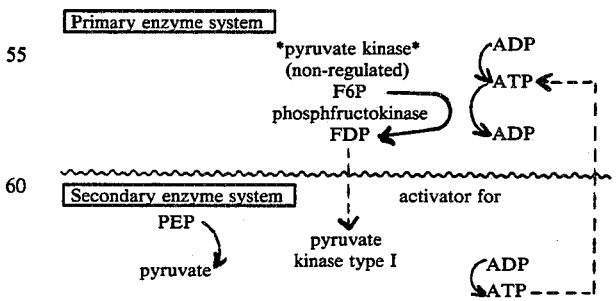

As soon as the primary enzyme (non-regulated pyruvate kinase) produces some ATP, phosphofructokinase is able to produce fructose-1,6-diphosphate (FDP), which in turn activates the FDP-sensitive pyruvate kinase (which is preferably present in relatively high concentrations). This pyruvate kinase, too, converts ADP to ATP which, if both primary and secondary enzyme systems are allowed to react together in one vessel, further increases the production of FDP by phosphofructokinase. This leads to augmented stimulation of the FDP-sensitive pyruvate kinase, and a substantially explosive increase in the production of pyruvate from phosphoenolpyruvate. The pyruvate can be converted to lactate by lactic dehydrogenase, with concommitant oxidation of NADH which can be followed photometrically. Alternatively, the pyruvate can be reacted with DNP-hydrazine to give a coloured end product.

An example of a system in which the modulator, once produced by the primary enzyme system, is self-producing, is that involving the conversion of complement factor C3 to C3b as follows:

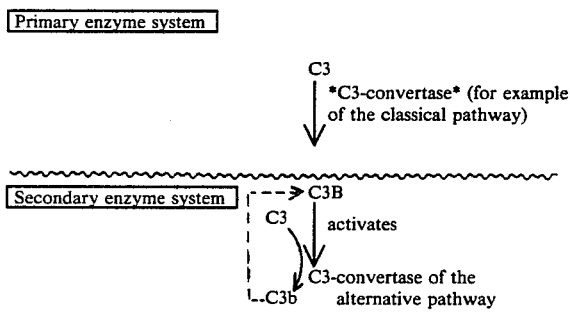

Complement component C3 is cleaved proteolytically to form the fragments C3b and C3a. There are two distinct C3-convertases which can do this: that of the so-called classical pathway of complement activation and that of the alternative pathway. Significantly, the latter is unlike the former in that it requires C3b itself to function.

In the reaction scheme shown above, the C3b formed by the independent C3-convertase, in activating the dependent convertase, results in an increase in the formation of C3b. This positive feed-back system would operate until maximal activation was achieved and very much more C3b was being produced than by the primary system alone. Either C3, C3b, C3a or the biological effects of these mediators in, for example, cell lysis or provocation of anaphylactoid reactions can be followed to indicate presence of the primary enzyme system.

As indicated above, the primary enzyme system may produce a regeneratable substrate for a secondary system. In this case, a secondary enzyme system may comprise two or more enzymes. Preferably one of the enzymes produces or uses a substance that is readily determinable. A two-enzyme system is, for example, as set out schematically below:

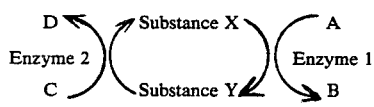

Substance X is the product of the primary enzyme system. The secondary enzyme system should be selected so that there is build-up of at least one of B and D and/or a decrease in at least one of A and C (insofar as they exist), as X recycles via Y. Provided suitable amounts of A and C are present, substance X will be continually recycled, using one molecule of each of A and C per cycle and producing one molecule of each of B and D. At least one of A, B, C and D is preferably readily determinable itself or may participate in one or more further reactions to give a determinable product or to use a determinable substrate. More than two enzymes may be combined in larger cycles or in interconnecting cycles. Alternatively, substance Y may be the product of the primary enzyme system. (In either case, the cycle may be reversed, if desired.)

An example of a system described in general terms above is that in which the secondary enzyme system comprises fructose diphosphatase and phosphofructokinase.

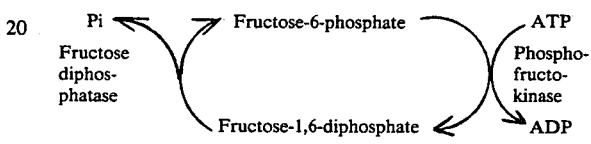

It is possible to determine the production or consumption of any of ATP, ADP and inorganic phosphate (Pi).

The primary enzyme system for the above secondary enzyme system should be one that is capable of producing either fructose-6-phosphate or fructose-1,6-diphosphate. Fructose-6-phosphate may be produced by a primary enzyme system in which phosphoglucomutase is the primary enzyme, converting glucose-1-phosphate to glucose-6-phosphate, which is then converted by phosphoglucoisomerase to fructose-6-phosphate. Fructose-6-phosphate may also be produced from glucosamine-6-phosphate by glucosamine-6-phosphate deaminase. Fructose-1,6-diphosphate may be produced from glyceraldehyde-3-phosphate and dihydroxyacetone phosphate by the action of aldolase, to enter the cycle at the bottom.

A further example of a substrate cycle used in a secondary enzyme system is one following:

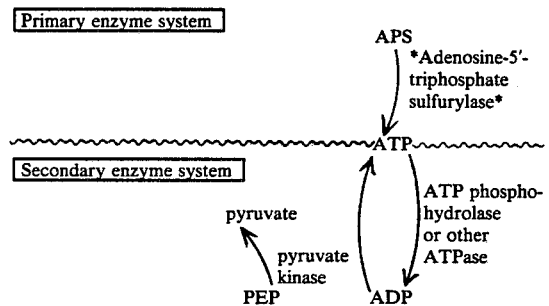

(Adenosine-5'-triphosphate sulfurylase converts adenosine-3'-phosphate-5'-phosphosulphate to ATP and SO₄.) Alternative enzymes for the production of ATP in the primary system are, for example, pyruvate phosphate dikinase, which catalyses the following reaction:

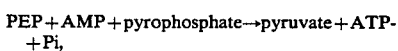

PEP+AMP+pyrophosphate→pyruvate+ATP-+Pi, and ATP:D-ribose-5-phosphate pyrophosphotransferase, which converts AMP and 5-phosphoribose-1-pyrophosphate to ATP and D-ribose-5-phosphate.

This system may be modified and extended, providing an example of a system involving both a substrate cycle and a modulated enzyme:

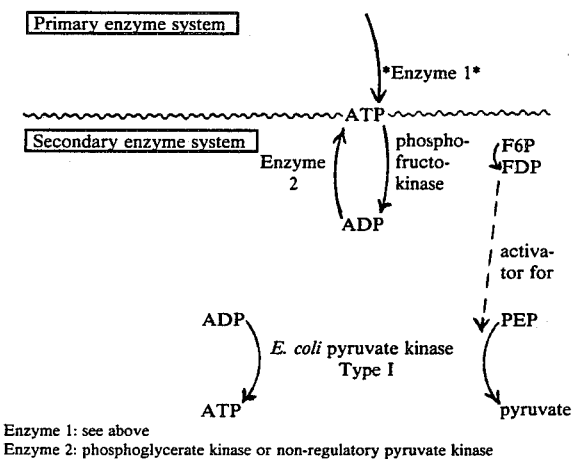

Enzyme 1: see above
Enzyme 2: phosphoglycerate kinase or non-regulatory pyruvate kinase The third reaction is preferably carried out separately from the second reaction.

A system involving regeneratable coenzyme is directly analogous to a system involving a regeneratable substrate as described in general terms above.

An example of such a system is the following, in which NADP is the regeneratable coenzyme:

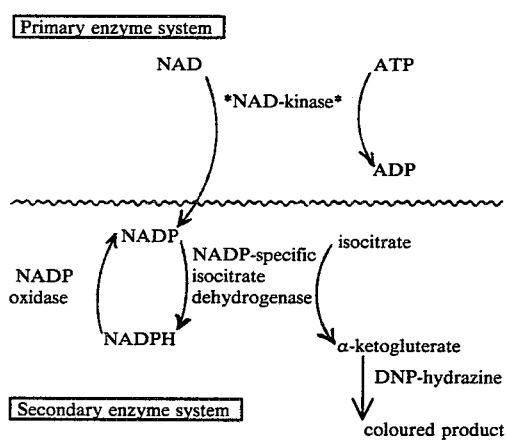

As mentioned above, a modulator, for example, a substrate or coenzyme, may take part in a secondary enzyme cycle in which not all the reactions are enzyme-catalysed. A simple example of such a system is as follows:

Uncatalysed chemical reaction

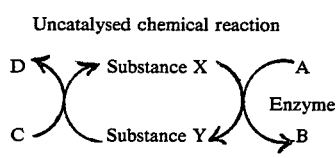

Either substance X or substance Y may be the product of the primary enzyme system. An advantage of such a system is that it may be possible to use a total of only two enzymes: one in the primary enzyme system and one in the secondary system.

An example of a group of reactions that may participate in such a cycle are oxidation-reduction reactions, for example, involving NAD/NADH or NADP/NADPH interconversions. An example of such a cycle is given below:

Uncatalysed chemical reaction

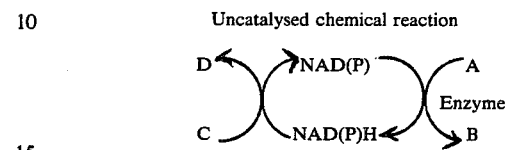

Substances capable of reduction with concommitant oxidation of NAD(P)H are well known, for example, 3'-(4,5-dimethylthiazolyl-2)-2,5-diphenyltetrazolium (MTT tetrazolium) is particularly useful, because on reduction it gives a blue coloured product and, moreover, the results are linear with regard to the NAD(P). A secondary enzyme cycle involving an NAD(P)/NAD(P)H interconversion may therefore be determined directly.

In the case of secondary enzyme cycles involving NAD(P)/NAD(P)H interconversions, it is preferable to use a primary enzyme system capable of producing NAD or NADP, for example, NADP may be produced from NAD by NAD-kinase, and NAD may be produced from NAD-dihydroxyacetone+nicotinamide by NADase (DPNase). Examples of such cycles are given below:

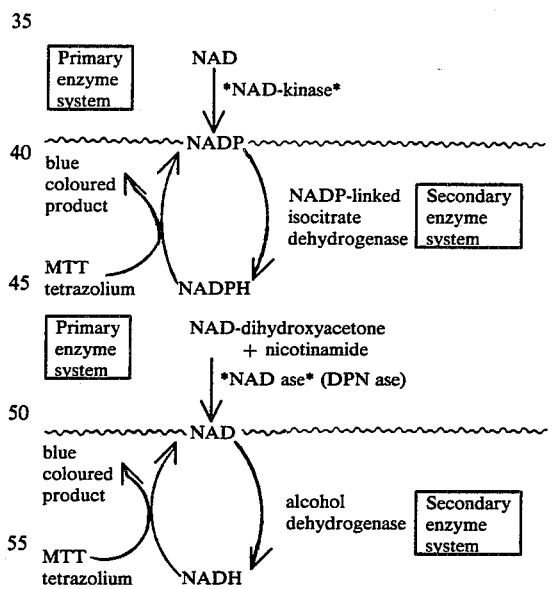

A modulator may moreover, take part in a secondary system that does not comprise any enzymes. In such a case, the modulator is a substrate or cofactor for a cycle in which the modulator is regenerated, so there is no net consumption thereof (cf the wholly and partly catalysed cycles mentioned above). A possible example of such a cycle is that in which the primary enzyme is peroxidase, which removes iodine (in the form of iodide ions) from thyroxine. The iodide ions may then be recycled in the secondary system via iodine, eg as follows:

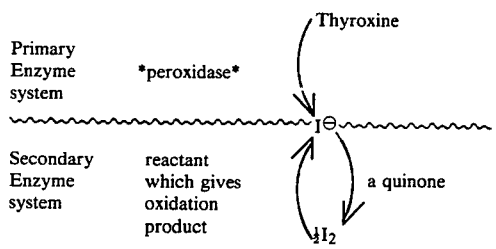

Alternatively, use may be made of a system using an iodide-iodine cyclic reaction (see Clinical Chemistry principles and Techniques, R. J. Henry, Harper & Row, New York 1964, p. 7) as follows:

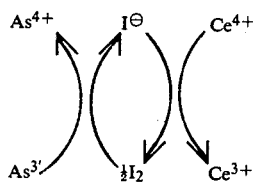

As indicated above, the modulator may be physically separated from the secondary system, the primary enzyme system causing the modulator to become available. The modulator may be an activator or inhibitor or an regeneratable substrate or co-factor. Metal ions are examples of modulators that may be compartmentalised. Metal ions are modulators for a number of enzymes, for example $Mg^{2+}$ and $Mn^{2+}$ are modulators for pyruvate kinase and isocitrate dehydrogenase.

The modulator may be present in relatively high concentrations in, for example, a synthetic or semi-synthetic vesicle or an organelle or cell, or may simply be present in a normal cell. The primary enzyme system may rupture or lyse the vesicle or cell, or may simply make it more permeable, to the modulator at least, so that there is leakage of sufficient amounts of modulator to affect the secondary system.

The use of lysozyme and trypsin my be particularly suitable for the disruption of cells, organelles, and vesicles. Either lysozyme or trypsin may be bound in the desired conjugate with the other being present in the reaction medium for disruption of the structure. In general, the trypsin is preferably bound in the conjugate, with higher concentrations of lysozyme in the reaction medium.

Lysozyme itself is capable of lysing the microorganism *Micrococcus lysodeiktus*. This microorganism may therefore be used as such or may have its internal concentration of a modulator increased, to be ruptured as desired by a primary enzyme system comprising lysozyme as the primary enzyme.

The method of the invention may be used for detecting ligands and receptors of natural or non-natural origin. Immunoassays have wide application, in both clinical and non-clinical fields; they are particularly useful in any circumstance where it is necessary to detect and/or determine small or very small amounts of substances. Clinical uses include, for example, the detection and/or determination of blood group substances, of Australia antigen, of diseases of various microbial origins eg. diseases caused by viruses, bacteria or fungi, or parasitic diseases, of hormones, of substances that may be present under certain conditions, for example, during pregnancy, for example, pregnancy-specific proteins and foetal proteins in foetal material and even in maternal material eg. blood, or in association with certain malignant states, of antibodies associated with autoimmune diseases and certain cancers, and drugs. Immunoassays are particularly useful in forensic investigations, as the amounts of substances to be detected and/or determined is often very small. Drug detection, both in forensic investigations and in investigations associated with human and animal sporting events may be advantageously carried out by immunoassays. The method of the invention may be used for detecting any of the above substances, and also any other substance that can be detected and/or determined by an immunoassay.

Assays analogous to immunoassays, for the detection and/or determination of ligands and receptors other than antigen/antibody pairs are also useful clinically and otherwise. Such ligands are, for example, hormones, for example, insulin, glucagon, piuitary hormones eg. vasopressin, oxytocin and trophic hormones, steroid hormones and gastric hormones; chemical intermediates and signals in the nervous system, for example, acetylcholine, opiates and their analogues, naloxones and encephalins, chalones, developmental signals and cell interaction signals; other naturally occurring chemicals eg. histamine; and substances originating outside the body eg. viruses and toxins.

An assay for a substance that can be considered to be both an antigen and the partner for a non-antibody receptor may be carried out using either the corresponding antibody or the other receptor as partner. An immunoassay may have the advantage that the antibody can be obtained more readily and cheaply than the other receptor. Conversely, it may be difficult to raise an antibody to a particular antigen, in which case the use of the non-antibody receptor is preferable. An assay using a non-antibody receptor may be even more specific than an assay using an antibody against the corresponding ligand because a specific receptor generally binds at the active part of the ligand molecule, whereas the corresponding antibody usually binds at another part of the molecule, giving greater possibility of cross-reactions.

Antibodies and antigens have a specific affinity for each other; when, however, an antibody-antigen complex has been formed, this complex and complement factor C1q can form a ligand-receptor pair. Factor C1q may therefor be used in an assay of the invention to detect antibody-antigen complexes of any type.

The assay technique to be used in the method of the invention is any immunoassay or analogous technique in which a labelled ligand or receptor is used as one of the components. The assay may be qualitative, quantitative or semiquantitative. Such assay techniques are well known, and include, for example, competitive binding techniques, so-called "sandwich" techniques, and any modifications thereof, for example, techniques which use competitive binding and "sandwich" techniques together in one assay. (The term "sandwhich" techniques as used herein includes so-called "antiglobulin" assays.)

In a competitive binding assay there is, for example, competition between the unknown amount of one component and a standard amount of the same component for a standard amount of its complementary component. One of the known components is generally bound to a solid matrix, whereby it can be readily isolated and one of the known components is generally labelled in some way.

In one method of carrying out a competitive binding assay, a calibration curve may first be set up as follows: An antigen is bound to a solid matrix and then allowed to come into contact with a solution containing its specific antibody. The antibody is then taken out of solution onto the matrix, and if the antibody or antigen is labelled, measurement of label of the material on the matrix gives a measure of the amount of specific antibody-antigen combination that has taken place. This combination may be interfered with in a modification of this method, by first mixing the antibody with the same, but soluble, antigen. If a large excess of soluble antigen is used the antibody binds this and thus remains in solution with its specific antigen-binding sites saturated and therefore unable to bind with matrix-linked antigen. Substantially no labelling will then appear in specific association with the solid matrix. Less than saturating amounts of soluble antigen will result in more free antibody available for combination with matrix-linked antigen. The system can therefore be calibrated in terms of soluble antigen and then used to determine quantitatively amounts of antigen present in "unknown" samples.

Alternatively, the assay may be organised conversely such that the amount of antibody remaining in solution after the addition of matrix-bound antigen is that which is quantitated.

Assays using a ligand and a non-antibody receptor are carried out in a directly analogous manner, using the ligand as the antigen and the receptor as the antibody.

Generally, "sandwich" techniques are based on the following: one component of an ligand-receptor couple, (generally bonded to a solid matrix), is contacted with the sample containing an unknown amount of the component to be determined. This, bound to the first component (and generally matrix-linked via the first component), is determined by the use of a further sample of the first component (which has been labelled in some way, and is not matrix bound), or a third component that has specific affinity for the component to be determined and that is itself labelled. (The chain may be longer than this.)

In a "sandwich" assay using a ligand and non-antibody receptor, either the ligand or the receptor may be matrix-bound. If the receptor is matrix-bound, then a further sample of that receptor may be used after the ligand has been bound thereto, or a mixed assay may be carried out, ie. the receptor is matrix-bound, the ligand is bound thereto, and then labelled antibody against the ligand, is used to detect the bound ligand.

"Sandwich" techniques have certain advantages over competitive binding techniques, for example, further amplification may be achieved because there will often be more than one receptor site for the conjugated enzyme to bind, so more than one molecule can bind per molecule of substance to be determined, thus increasing the sensitivity of the assay.

A further advantage of sandwich techniques is that it may be possible to use a standard enzyme conjugate, which may simplify the determination and is often more convenient when carrying out assays for different substances. An example of a system using a standard conjugate is that in which a sheep antibody against the antigen to be determined is bound to a solid matrix, the antigen to be determined is then contacted with the sheep antibody, free antigen is removed, a goat antibody against the antigen is contacted with the antigen, freely antibody is removed, and finally a standard labelled antibody with specificity for the antigenic determinants on goat antibodies is contacted with the goat antibody.

After an assay has been carried out according to the chosen technique or mixture of techniques, it is usually necessary to separate the portion of enzyme conjugate that is to be assayed from the portions of enzyme conjugate that are present in the assay reaction mixture but are not to be assayed. This is facilitated by the conjugate being bound, during the assay, to an insoluble matrix.

The matrix may be, for example, Sephadex, a plastics material eg. nylon, cellulose or a derivative thereof, for example, bromoacetylcellulose (cf. Self et al, loc cit). Some receptors, both antibodies and other receptors, may be cell-associated in vivo; some antibodies are present on cell surfaces, some receptors are also associated with cell surfaces, and some receptors are presaent inside cells. Cell-associated receptors of any type may be used after isolation and purification, or they may be used in association with all or part of the cell ie. already matrix-bound.

Generally, the matrix-bound conjugate is assayed, but that portion of the conjugate left in suspension may be assayed.

The enzyme bound in the conjugate is then generally allowed to catalyse the appropriate reaction. If two or more reactions are required to modulate the secondary system, these may be carried out simultaneously or successively as separate reactions, in each case in situ or in different reactions vessels. The reaction(s) catalysed by the secondary system may also be carried out simultaneously with those of the primary enzyme system (ie. on modulation by the primary enzyme system) or as separate reaction(s) and may be carried out in situ or in another reaction vessel.

It is often preferable to allow the primary enzyme sytem to react for a predetermined time, and then to allow the modulator to contact the secondary system for a predetermined time. As mentioned above, separating the primary and secondary systems makes it more easy to obtain quantitive results and gives greater freedom in the choice of enzymes.

It is also possible, in some cases, to release the primary enzyme from the enzyme conjugate after the portion of enzyme conjugate to be assayed has been isolated, for example, if the enzyme is bound in the conjugate by disulphide bonds, it may be released by the action of dithiothreitol. If this is done, the free enzyme is reacted subsequently as described above for enzyme conjugates.

In general it is perferred to have the secondary system primed, that is to say, to have all the components present in optimal amounts and under optimal reaction conditions so that the presence or removal of the appropriate modulator will result in an immediate and optimal reaction. In some cases, however, it may be desirable to delay the action of the secondary system. This may be done by not combining the product of the primary system (the modulator) with the secondary system, or by omitting one or more of the components of the secondary system. Addition of the missing component will then initiate the reaction.

A conjugate of the invention may be bound to a micro-titre plate, a test strip or dip stick. In the former case, the whole reaction sequence may be carried out on the plate. Microtitre plates are well known in the art, and ones suitable for application in previously proposed enzyme immunoassays (Elisa, or Enzyme-linked Immunosorbent assays) are available commercially. Test strips and dip sticks are also known.

In the method of the present invention, the enzyme conjugate may be determined in situ ie. each of the reactions, starting with that catalysed by the primary enzyme, may be carried out on the micro-titre plate.

Test strips and dip-sticks may be used analogously to micro-titre plates.

A kit comprising components suitable for carrying out an immunoassay of the invention is also part of the present invention.

A conjugate of the invention may be prepared by any method suitable for binding ligands and enzymes or receprors and enzymes. Such methods are well known and often utilise bifunctional agents. The two components are preferably bonded such that the ligand-receptor binding sites on ligands and receptors are not substantially impaired, and also that the active site of the enzyme is not inactivated.

As has been explained hereinbefore, the modulator for the secondary system may serve to activate the secondary system by its production or serve to activate the secondary system by its removal if it is an inhibitor. Of these two alternative methods it is generally most desirable that the modulator activates the secondary system when it is produced by the primary system. Thus a favoured method of this invention comprises carrying out an assay for the ligand or receptor, the assay requiring a conjugate between the ligand or receptor and a primary enzyme that is itself capable of producing a modulator for a secondary system and determining that portion of labelled component to be determined by allowing the primary enzyme to function so that said modulator is produced, whereby the secondary system is caused to function, and determining a product of the secondary system.

As previously indicated herein the method of this invention is particularly suitable when adapted for the determination of an antigen. Also as previously indicated herein the method of this invention is particularly suitable when adapted for the determination of an antibody.

As previously indicated the amplification achieved in the method of this invention occurs because the secondary system produces substantially more molecules of detectable substance than are produced by the primary system once it is "switched on" by the primary system. Particularly rapid rises in the presence of the detectable product of the secondary system can occur when the secondary system is capable of regenerating a substrate or co-factor (i.e. a modulator) for the secondary system that is produced by the primary enzyme system This aspect of the invention in which the modulator is a substrate or co-factor for a secondary system that is capable of generating the substrate or co-factor is particularly favoured. Yet more favourably in this form of the invention the secondary system comprises a cycle capable of generating the substrate or co-factor. Systems which can be adapted to favourable purposes include (a) a primary system comprising phospofructokine and a secondary system comprising pyruvate kinase type I and (b) a primary system comprising phosphofructokinase and non-regulated pyruvate kinase and the secondary system comprises pyruvate kinase type I.

As hereinbefore indicated the modulator may be generated in this invention in (a) a secondary system comprising one enzyme catalyzed reaction and one non-enzyme catalyzed chemical reaction (b) a secondary system that does not comprise any enzyme catalyzed reactions or (c) a secondary system comprising two enzyme catalyzed reactions.

As previously indicated particularly apt systems for use in this invention comprises oxidation/reduction systems, of which those employing NAD/NADH interconversions and NADP/NADPH interconversions are most suitable.

As made apparent hereinbefore, the method of this invention is most aptly performed using systems in which the secondary systems has all components present except the modulator in optimal amounts before the modulator is allowed to control the secondary system. (In this aspect the modulator will not be an inhibitor).

A further example of a secondary system which generates more of the modulator which is produced by the primary system may be represented thus:

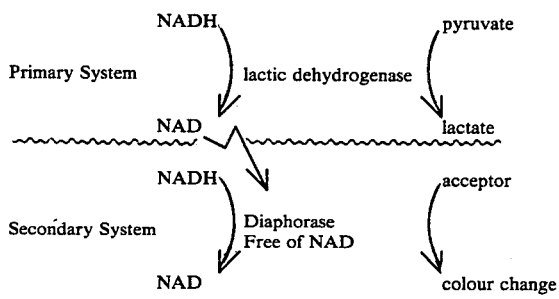

The secondary system is switched on by the NAD produced by the primary system (Diaphorase depleted of its bound NAD is inactive). The acceptor may be a molecule which is reduced on operation of the secondary system in a readily detectable manner, for example, by changing colour in the case of methylene blue or 2,6-dichlorophenol-indophenol. (Analogous primary systems may be employed in which the LDH and its substrate is replaced by another enzyme and its substrate).

The following abbreviations are used in the present specification:
G1P, glucose-1-phosphate;
G6P, glucose-6-phosphate;
F6P, fructose-6-phosphate;
FDP, fructose-1,6-diphosphate;
ATP, adenosine triphosphate;
ADP, adenosine diphosphate;
AMP, adenosine monophosphate;
PEP, phosphoenolpyruvate;
NAD, nicotinamide adenine dinucleotide;
NADH, reduced NAD;
PGM, phosphoglucomutase;
PGI, phosphoglucose isomerase;
PFK, phosphofructokinase;
PK, pyruvate kinase;
LDH, lactic dehydrogenase;
FDPase, fructose-1,6-diphosphatase;
DNP, dinitrophenol;
NADP, nicotinamide edenine dinucleotide, phosphate;
NADPH, reduced NADP;
APS, adenosine 3'-phosphate-5'-phosphosulphate.

The following Examples illustrate the invention.

EXAMPLE 1

(a) Preparation of Pyruvate Kinase Extract

Cultures of E.coli strain Kl-1 were grown on a synthetic medium containing essential nutrients and glycerol as carbon source, until well into their logarithmic phase of growth. The cells were harvested, washed by centrifugation and resuspended in a sonication buffer of 5 mM phosphate, 1 mM EDTA, 2 mM mercaptoethanol pH 7.5 in an amount of approximately 20 mg dry weight per ml. They were then disrupted with an MSE ultrasonic disintegrator for 4 minutes. The resulting crude extract was separated from cell debris by centrifugation. As well as containing pyruvate kinase (PK) this extract also contained an interfering isoenzyme of PK with different properties, and also a number of other enzyme activities which interfered with the determination. It was found, however, that it was possible to remove all of these contaminating activities simply by heating the extract to 55° C. for 20 minutes. This heat-treated extract was used in this Example.

(b) Preparation of the Immunoabsorbent

Bromoacetyl cellulose conjugated human serum albumin BAC-HSA was prepared exactly as described in Solid Phase Assay of Radioactive Antibody to Soluble Antigens by Self, C. H., Tew, J. G., Cook, R. D. and Stavitsky, A. B. (1973) in Immunochemistry, 11, 227–233.

(c) Preparation of the Enzyme-Antibody Conjugate

This was based on Protein thiolation and reversible protein-protein conjugation. N-Succinimidyl 3-(2-pyridyldithio)propionate a new heterobifunctional reagent by Carlsson, J., Drevin, H., Axen, R. (1978) in Biochem. J., 173, 723–737.

Both the enzyme (phosphofructokinase "PFK", which had been prepared from Stearothermophilis and purified to crystalline purity by means of AMP and ATP affinity chromatography) and the antibody (IgG, obtained from Miles-Yeda Ltd., Rehovot, Israel), were prepared for conjugation by separate passage through a Sephadex G-25 (fine) column equilibrated with the "coupling buffer" of 0.1M sodium phosphate pH 7.5 containing NaCl at 0.1M. One mg of each protein was applied. One ml of the IgG eluant of optical density at 280 nm of 0.67 O.D. units was taken, shaken gently while a five-fold molar excess of the conjugating agent (N-succinimidyl 2-(2-pyridyldithio) propionate, "SPDP") was added from a stock solution (5 mM) in ethanol. The mixture was allowed to stand for 30 minutes at 23° C. with occasional shaking. Then with rapid stirring, 1 ml of the PFK eluant, also of optical density at 280 nm of 0.67 O.D. units, was added. The mixture was allowed to remain at room temperature for 24 hours. During this time the newly introduced labile disulphide groups on the IgG underwent exchange reactions with the pre-existing reactive thiol groups on the PFK to give rise to PFK-IgG conjugates.

(d) Method of Assay

Into each of two small test tubes were put 20 μl of the PFK-IgG conjugate. Human serum albumin (0.1 ml of a 10 mg/ml solution) was added to one tube and bovine serum albumin (0.1 ml of a 10 mg/ml solution) added to the other. BSA was added to the second tube so that any non-specific protein effect on the conjugate would be duplicated in both tubes. The volumes of the tubes were then made up to a standard 1.0 ml with phosphate-buffered saline (PBS). The contents of the tubes were mixed and incubated at 37° C. for 15 minutes. They were then added separately to two aliquots of BAC-HSA (each 0.1 ml of the standard suspension which had been washed 4 times in PBS) in micro-centrifuge tubes. The capped tubes were then shaken and incubated at 37° C. for a further 15 minutes. They were then centrifuged in a micro-centrifuge at full speed for one minute, the supernatant solution discarded, the solid washed by the addition of 1.5 ml of PBS to each tune, the contents mixed on a vortex mixer and centrifuged as above. The washing procedure was repeated 4 times to ensure removal of unbound contaminating PFK. To each tube was then added 0.94 ml of the assay buffer (10 mM dimethylglutarate pH 6.8, 5 mM, MgCl$_2$) and then 50 μl of a 40 mM solution of fructose 6-phosphate and 10 μl of a 40 mM solution of adenosine triphosphate. The contents of the tubes were mixed by means of the vortex mixer and then incubated with gentle shaking at 37° C. for two and a half hours. After this the tubes were once more centrifuged at full speed for one minute and the supernatant solutions taken off and assayed for evidence of previous PFK activity in the tubes during the two and a half hour incubation. The particular system enabled a direct comparison to be made between the triggered amplifier method of the present invention and a conventional 1:1 coupled enzymic detection method. For the former, the supernatant solution was tested for its ability to activate a primed PK assay set-up without FDP. For the latter the ADP produced concomitantly with the FDP was assayed by following the NADH oxidation it produced in a directly coupled pyruvate kinase—lactate dehydrogenase system set-up to operate optimally (with added FDP) but without ADP. The two assay systems were, therefore, composed as shown in Table 1.

TABLE 1

| Assay components for the ADP and FDP assays | | |
|---|---|---|
| Component | Primed amplifier (FDP determining) | Conventional coupled (ADP determining) |
| NADH | 0.1 mM | 0.1 mM |
| LDH (Lactate Dehydrogenase) | 14.4 units | 14.4 units |
| PK(I) extract | 10 μl | 10 μl |
| PEP § | 2.0 mM | 2.0 mM |
| ADP | 2.0 mM | NIL |
| FDP | NIL | 1.0 mM |
| ATP | 0.4 mM | 0.4 mM |
| supernatant solution | 100 μl | 100 μl |
| assay buffer | to 1 ml | to 1 ml |

§The maximal amount of PEP was used which could be added without causing unwanted background activation of the pyruvate kinase in the FDP-determining assays.

Results (i) Primed amplifier (FDP-dependent) assy.

This was set up such that full activation of the system produced a rate of oxidation of NADH of 7.9 nmoles/min (a convenient rate to measure).

The results of adding 100 μl of the supernatant solution from the immunoabsorbents either previously exposed to HSA or BSA are shown in Table 2.

TABLE 2

| supernatant | Primed amplifier (FDP-dependent) assay results |
| --- | --- |
|  | rate of NADH oxidation |
| from BSA-exposed tube | 4.8 nmoles/min (61% maximal) |
| from HSA-exposed tube | nil |

(ii) Conventional-coupled (ADP-dependent) assay.

The results of adding 100 μl of either supernatant solution to the ADP-dependent system are shown in Table 3.

TABLE 3

| supernatant | Conventional-coupled (ADP-dependent) assay results |
| --- | --- |
|  | rate of NADH oxidation |
| from BSA-exposed tube | 0.12 nmoles/min. (1.6% maximal)§§ |
| from HSA-exposed tube | nil |

§§This figure on repeated assays was close to background and difficult to quantitate accurately.

The results show clearly that:

(a) the PFK-IgG conjugate was inhibited in its binding to BAC-HSA by HSA much more than by BSA.

(b) the sensitivity of the primed-amplifier system was much higher than the conventional-coupled reaction.

EXAMPLE 2

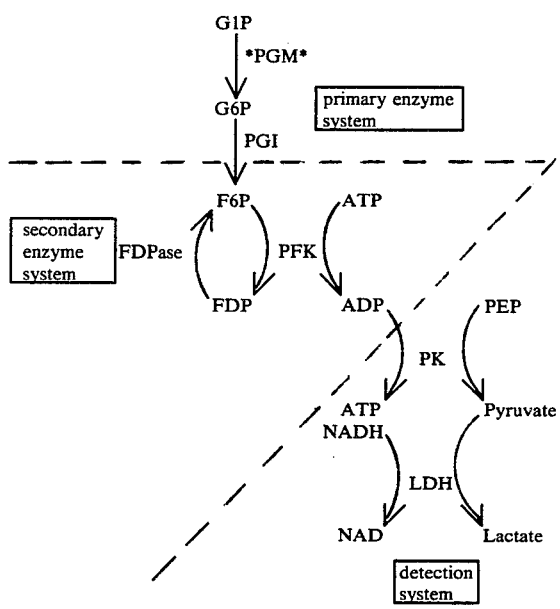

The reaction sequence is outlined above. Phosphoglucomutase (PGM) was chosen to be the enzyme to be linked to an antibody. The presence of the antibody is determinable by the ability of the conjugate to catalyse the formation of G6P from G1P. This in the presence of phosphoglucose isomerase (PGI) results in the sequential formation of F6P which is then itself acted upon by phosphofructokinase (PFK) to give FDP. This latter reaction generates one molecular of ADP from ATP for every molecule of F6P converted to FDP. The final detection system shown in the diagram takes advantage of this, in that it is dependent on ADP. This system results in oxidation of NADH which is monitored spectrophotometrically by the concomitant decrease in optical density of the mixture to ultraviolet radiation of 340 nm.

The secondary enzyme cycle operates as follows. In the presence of fructose diphosphatase (FDPase) the FDP genarated by the system, and which otherwise would play no further part in the system, is reconverted into F6P (without involvement of ADP/ATP) and is thus available again for a further turn of the cycle, to give rise to another molecule of ADP for each turn of the cycle.

The amplification of the activity of PGM achieved by the catalytic secondary enzyme cycle may be readily seen by comparing the NADH oxidation resulting from the corresponding 1:1 linked enzyme system which does not have FDPase present ie. in which $F_6P$ is not recycled.

Method of enzyme assay

All determinations were performed using 1 ml quartz cuvettes with a path-length of 1 cm. NADH oxidation was monitored by the decrease in absorbance at 340 nm. The reactions were carried out in a buffer comprising: 25 mM Tris-HCl, 10 mM $MgCl_2$, 1 mM EDTA at pH 8.00 and 30° C. The final reaction mixtures were as shown in Table 4. LDH and PK were obtained from Boehringer Mannheim and the other enzymes from the Sigma Chemical Company.

Results of enzyme assays

These are shown in FIG. 4 and represent the activities of the systems after they had been incubated for 12 minutes at 30° C., after initiation.

The results indicate that:

(i) the basic 1:1 linked enzyme reaction sequence worked (compare first to third column), (ii) the catalytic substrate cycle formed by inclusion of FDPase into the system markedly increased the activity of the system for the standard amount of PGM (column two).

(iii) the background activity of the total system, including the substrate cycle, in the absence of PGM is very low (column three).

TABLE 4

| components§ | 1:1 linked (no cycle) | including cycle | no PGM (back-ground) |
| --- | --- | --- | --- |
| NADH | 0.1 mM | 0.1 mM | 0.1 mM |
| ATP | 0.4 mM | 0.4 mM | 0.4 mM |
| PEP | 2.0 mM | 2.0 mM | 2.0 mM |
| G1P | 2.0 mM | 2.0 mM | 2.0 mM |
| LDH | 1.1 U | 1.1 U | 1.1 U |
| PK | 0.04 U | 0.04 U | 0.04 U |
| PGI | 0.2 U | 0.2 U | 0.2 U |
| PFK | 0.02 U | 0.02 U | 0.02 U |
| FDPase | NONE ADDED | 0.1 U | 0.1 U |
| PGM | 0.06 U | 0.06 U | NONE ADDED |
| oxidation rate of NADH (n mole/minute) | 0.475 | 4.72 | 0.064 |

'U' stands for units of enzyme activity. However as different conditions were used to measure each enzyme by their various manufactures the various activities do not necessarily correspond to each other in the final assay mixtures but simply denote the standard amounts of each preparation used.
§Assay buffer of 25 mM Tris-HCl, 10 mM $MgCl_2$, 1 mM EDTA, at pH 8.00 added to each assay to a final volume of 1.00 ml.

Linking the substrate cycle to antibody-antigen reactions.

After demonstrating the amplification afforded by the substrate cycle as above, the usefulness of the system in detecting antibody (or antigen) was assessed. This was done by conjugating the primary enzyme, PGM, to IgG with specificity against human serum albumin.

Formation of the Conjugate

As in Example 1, the heterobifunctional linking reagent SPDP was used, however in this instance both enzyme and antibody were treated before conjugation.

One mg of the IgG (Miles-Yeda Ltd) was passed through a Sephadex G-25 column previously equilibrated with the 'coupling-buffer' (0.1M sodium phosphate pH 7.5 containing 0.1M NaCl). The antibody eluted from the column was then shaken gently with a ten-fold excess of SPDP which was added from a 5 mM stock solution in ethanol. The mixture was allowed to stand for 30 minutes at 23° C. with occasional shaking. It was then passed through another Sephadex G-25 column, this time equilibrated with 0.1M sodium acetate at pH 4.5 containing 0.1M NaCl. The protein fraction of the eluant was taken an equal volume of 100 mM dithiothreitol was added with rapid stirring. The mixture was left for 20 minutes at 23° C. after which it was passed through another Sephadex G-25 column equilibrated with the original 'coupling buffer'.

At the same time, 1 mg of PGM was passed through a G-25 column equilibrated with coupling buffer. The major protein band of the eluant was then exposed to a ten-fold excess of SPDP as above and left also for 30 minutes at 23° C. It was then mixed rapidly with the treated antibody and left to stand for 2 hours at 23° C. to allow the conjugate to form.

Full Conjugate Assay

Into each of two small test tubes were put 0.2 ml of the PGM-IgG conjugate. Human serum albumin (0.1 ml of a 10 mg/ml solution) was added to one tube and the same amount of bovine serum albumin to the other; 0.7 ml of phosphate-buffered saline (PBS) was then added to both tubes and the contents mixed and incubated at 37° C. for 15 minutes. They were then added separately to two aliquots of BSA-HSA (each 0.1 ml of the standard suspension which had been washed 4 times in PBS) in micro-centrifuge tubes. The capped tubes were then shaken and incubated at 37° C. for a further 15 minutes. They were then centrifuged in a micro-centrifuge at full speed for one minute, the supernatant solution discarded, the solid washed by the addition of 1.5 ml of PBS to each tube, the contents mixed on a vortex mixer and centrifuged as above. The washing procedure was repeated 4 times to ensure removal of unbound contaminating PGM. To each tube was then added 50 μl of a 40 mM solution of glucose-1-phosphate and assay buffer (25 mM Tris-HCl, 10 mM MgCl₂, 1 mM EDTA, pH 8.00) to a final volume of 1 ml. The contents were mixed and then incubated with gentle shaking for two and a half hours at 37° C. After incubation, the tubes were centrifuged at full speed for one minute and the supernatant solutions taken off with Pasteur pipettes and the contents assayed for evidence of PGM activity during the two and a half hour incubation. They were assayed in two ways. By the direct 1:1 linked enzyme sequence outlined above and also by the sequence including the secondary enzyme cycle (FDPase included). The assays were set up as previously described but included 0.2 ml of the superanatant solutions and thus 0.2 ml less of the separately added assay buffer in each case.

Results

These are shown in Table 5. They show two features:
(i) that the substrate cycle inclusion into the assay provides for much greater activity of the system for a given amount of conjugate.
(ii) that the system is capable of showing the inhibition of uptake of the conjugate onto BAC-HSA by soluble HSA as against the control of BSA.

TABLE 5

| Activities of BAC-HSA bound PGM-IgG conjugates in terms of final NADH oxidation (in n moles/minute) | | |
|---|---|---|
| supernatant | without substrate cycle | with substrate cycle |
| HSA-exposed tube | 0.19 | 2.21 |
| BSA-exposed tube | 0.36 | 5.07 |

EXAMPLE 3

Detection of Pyruvate Kinase (II)

In order to demonstrate the enhancement in sensitivity brought about by the method of this invention an assay for pyruvate kinase (II) was carried out with and without a secondary system to produce amplification. The two assays may be represented as follows:

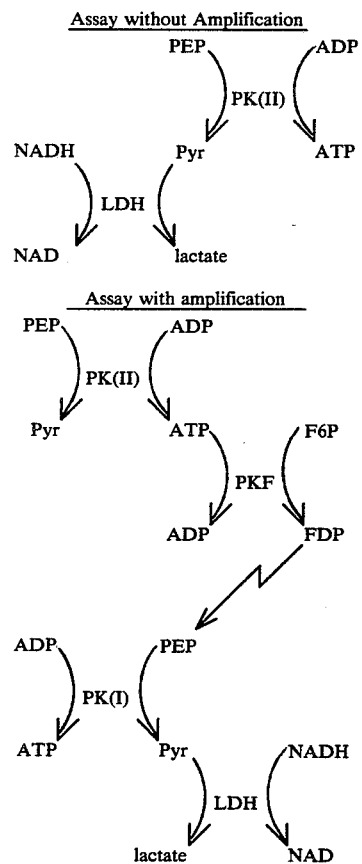

In the assay system without amplification PK(II) converts PEP and ADP into pryuvate and NAHD to NAD and lactate. The change in concentration of NADH can be monitored by absorbence at 340 nm.

In the assay system with amplification (that is the assay incorporating the secondary system) the preceeding sequence takes place but in addition the secondary system generates ATP. In this amplified system, in addition to the PEP, ADP, NADH, PK(II) and LDH present in the nonamplified system, the following are also present: F6P, PFK and PK(I). In the presence of ATP (generated by primary cycle) the PFK converts the F6P into FDP. The FDP activates the PK(I) which then is available to a convert the PEP and ADP to ATP and pyruvate. The ATP thus produced feeds back with the secondary system and the pyruvate is converted into lactate by LDH in the presence of NADH. This end reaction is monitored at 340 nm as in the unamplified assay.

To indicate the usefulness of this amplification method the PK(II) was initially assayed by the direct reaction as follows: The assay mix was as shown in Table 6 (left column) with a buffer consisting of 10 mM dimethylglutarate pH 6.8 5 mM $MgCl_2$. All assays were carried out at 30° C. The PK(II) was obtained from Calbiochem and, as a result of trials, a standard amount chosen which gave the activity shown in the Table. This amount was used for all following experiments. PK(I) was as in previous experiments.

The assay system including the positive feed-back amplifier was composed as shown on the right hand column of Table 6. The activity attribuatable to the addition of the same amount of PK(II) as before and after allowing the feedback system to get underway for seven minutes, is shown. The activity attribuable to PK(II) is raised eleven times over the direct method.

TABLE 6

|  | Direct assay | Feed-back assay |
|---|---|---|
| ADP | 0.4 mM | 0.4 mM |
| PEP | 1.0 mM | 1.0 mM |
| NADH | 0.1 mM | 0.1 mM |
| LDH | 1.1 U | 1.1 U |
| PK(II) | standard | standard |
| F6P |  | 2.0 mM |
| PFK |  | 1.0 U |
| PK(I) |  | 10 μl |
| Buffer | To 1.0 ml | To 1.0 ml |
| Rate of Change Absorbence (OD Units at 340 nm per 10 minutes) | 0.005 | 0.055 |

Using the direct method, the standard amount of PK(II) could just about be detected whereas it was quite readily detectable using the feed-back amplifier.

What I claim is:

1. In a method of determining a ligand or receptor in solution which comprises an assay wherein:
   (a) the presence of said ligand or receptor in said solution causes a conjugate in a solution to become matrix bound, said conjugate comprising a ligand or receptor labelled with an enzyme;
   (b) the matrix bound conjugate is separated from unbound conjugate, and
   (c) the matrix bound or the unbound conjugate is assayed,
   the improvement which comprises:
   (d) contacting the conjugate to be assayed with a precursor for a modulator for a cyclic chemical reaction whereby said modulator is produced as a result of reaction of label and precursor for the modulator, and
   (e) contacting the thus produced modulator with the components of a cyclic chemical reaction which is activated by the modulator, which cyclic chemical reaction interconverts said modulator and its reduced or oxidized form and which cyclic chemical reaction thereby regenerates the modulator produced by the conjugate and produces a determinable change, said components of the cyclic chemical reaction being present in sufficient quantity to maintain the cyclic chemical reaction and produce determinable product as the cyclic chemical reaction proceeds, whereby amplification occurs.

2. The improvement according to claim 1 wherein the modulator is a cofactor which the cyclic chemical reaction interconverts with its reduced form.

3. The improvement according to claim 2 wherein the cofactor is a nicotinamide adenine dinucleotide.

4. The improvement according to claim 2 wherein NAD is converted to NADH by a dehydrogenase.

5. The improvement according to claim 4 wherein the dehydrogenase is an alcohol dehydrogenase.

6. The improvement according to claim 4 wherein the conversion of NADH to NAD accompanies reduction of a tetrazolium compound whereby a colour change is produced.

7. The improvement according to claim 4 wherein the cyclic chemical reaction comprises two enzymatic reactions.

8. The improvement acccording to claim 1 wherein the ligand is an antibody or antigen.

9. The improvement according to claim 1 wherein the ligand in solution and conjugate are added sequentially.

10. The improvement according to claim 9 wherein the ligand in solution is added before the conjugate.

11. In a method of determining a ligand or receptor in solution which comprises an assay wherein:
   (a) a matric to which is bound a ligand or receptor is contacted with a conjugate and with the, said conjugate comprising a ligand or receptor labelled with an enzyme;
   (b) the matrix bound conjugate is separated from unbound conjugate, and
   (c) the matrix bound or the unbound conjugate is assayed,
   the improvement which comprises:
   (d) contacting the conjugate to be assayed with a precursor for a modulator for a cyclic chemical reaction whereby said modulator is produced as a result of reaction of label and precursor for the modulator, and
   (e) contacting the thus produced modulator with the components of a cyclic chemical reaction which is activated by the modulator, which cyclic chemical reaction interconverts said modulator and its reduced or oxidized form and which cyclic chemical reaction thereby regenerates the modulator produced by the conjugate and produces a determinable change, said components of the cyclic chemical reaction being present in sufficient quantity to maintain the cyclic chemical reaction and produce determinable product as the cyclic chemical reaction proceeds, whereby amplification occurs.

12. The improvement according to claim 11 wherein the modulator is a cofactor which the cyclic chemical reaction interconverts with its reduced form.

13. The improvement according to claim 12 wherein the cofactor is a nicotinamide adenine dinucleotide.

14. The improvement according to claim 12 wherein the NAD is converted to NADH by a dehydrogenase.

15. The improvement according to claim 14 wherein the dehydrogenase is an alcohol dehydrogenase.

16. The improvement according to claim 14 wherein the conversion of NADH to NAD accompanies reduction of tetrazolium compound whereby a colour change is produced.

17. The improvement according to claim 14 wherein the cyclic chemical reaction comprises two enzymatic reactions.

18. The improvement according to claim 11 wherein the ligand is an antibody or antigen.

19. In a method of determining a ligand or receptor in solution which comprises an assay wherein:
   (a) the presence of said ligand or receptor in said solution causes a conjugate in a solution to become matrix bound, said conjugate comprising a ligand or receptor labelled with an enzyme;
   (b) the matrix bound conjugate is separated from unbound conjugate, and
   (c) the matrix bound or the unbound conjugate is assayed,
   the improvement which comprises:
   (d) contacting the conjugate to be assayed with a precursor for a modulator for a cyclic chemical reactor whereby said modulator is produced as a result of reaction of label and precursor for the modulator, and
   (e) contacting the thus produced modulator with the components of a cyclic chemical reaction interconverts said modulator and a modified modulator which has more or fewer phosphate groups attached thereto, and which cyclic chemical reaction thereby regenerates the modulator produced by the conjugate and produces a determinable change, said components of the cyclic chemical reaction being present in sufficient quantity to maintain the cyclic chemical reaction and produce determinable product as the cyclic chemical reaction proceeds, whereby amplification occurs.

20. The improvement according to claim 19 wherein the modulator has one less phosphate group than the modified modulator.

21. The improvement according to claim 20 wherein the modulator is fructose-6-phosphate and the modified modulator is fructose-1,6-diphosphate.

22. The improvement according to claim 19 wherein the modulator has one more phosphate group than the modified modulator.

23. The improvement according to claim 22 wherein the modulator is ATP and the modified modulator is ADP.

24. The improvement according to claim 19 wherein the determinable product is inorganic phosphate.

25. The improvement according to claim 19 wherein the ligand is an antibody.

26. The improvement according to claim 19 wherein the ligand is an antigen.

27. In a method of determining a ligand or receptor in solution which comprises an assay wherein:
   (a) a matrix to which is bound a receptor or ligand is contacted with a conjugate and with the solution, said conjugate comprising a receptor or ligand labelled with an enzyme;
   (b) the matrix bound conjugate is separated from unbound conjugate, and
   (c) the matrix bound or the unbound conjugate is assayed,
   the improvement which comprises:
   (d) contacting the conjugate to be assayed with a precursor for a modulator for a cyclic chemical reaction whereby said modulator is produced as a result of reaction of label and precursor for the modulator, and
   (e) contacting the thus produced modulator with the components of a cyclic chemical reaction which is activated by the modulator, which cyclic chemical reaction interconverts said modulator and a modified modulator which has more or fewer phosphate groups attached thereto, and which cyclic chemical reaction thereby regenerates the modulator produced by the conjugate and produces a determinable change, said components of the cyclic chemical reaction being present in sufficient quantity to maintain the cyclic chemical reaction and produce determinable product as the cyclic chemical reaction proceeds, whereby amplification occurs.

28. The improvement according to claim 27 wherein the modulator has one less phosphate group than the modified modulator.

29. The improvement according to claim 28 wherein the modulator is fructose-6-phosphate and the modified modulator is fructose-1,6-diphosphate.

30. The improvement according to claim 27 wherein the modulator has one or more phosphate groups than the modified modulator.

31. The improvement according to claim 30 wherein the modulator is ATP and the modified modulator is ADP.

32. The improvement according to claim 27 wherein the determinable product is inorganic phosphate.

33. The improvement according to claim 27 wherein the ligand is an antibody.

34. The improvement according to claim 27 wherein the ligand is an antigen.

35. The improvement according to claim 27 wherein the ligand in solution and conjugate are added sequentially.

36. The improvement according to claim 27 wherein the ligand in solution is added before the conjugate.

* * * * *